United States Patent [19]

Harris

[11] Patent Number: 5,346,086
[45] Date of Patent: Sep. 13, 1994

[54] SHARPS DISPOSAL CONTAINER WITH A PIVOTED CLOSURE DOOR

[75] Inventor: John Harris, Gwent, United Kingdom

[73] Assignee: Frontier Plastics (South Wales) Limited, Gwent, United Kingdom

[21] Appl. No.: 30,405

[22] PCT Filed: Sep. 20, 1991

[86] PCT No.: PCT/GB91/01624
§ 371 Date: May 18, 1993
§ 102(e) Date: May 18, 1993

[87] PCT Pub. No.: WO92/05744
PCT Pub. Date: Apr. 16, 1992

[30] Foreign Application Priority Data

Sep. 27, 1990 [GB] United Kingdom ............... 9021075

[51] Int. Cl.⁵ .............................................. B65D 51/18
[52] U.S. Cl. ........................... 220/254; 220/281; 220/282; 220/307; 220/908; 206/364; 232/44
[58] Field of Search ............... 220/281, 212, 254, 282, 220/283, 307, 338, 908; 206/364, 365, 366; 232/44, 47, 62

[56] References Cited

U.S. PATENT DOCUMENTS

| | | |
|---|---|---|
| 3,322,477 | 5/1967 | Armijo . |
| 3,964,609 | 6/1976 | Perrella ........................... 206/540 |
| 4,203,529 | 5/1980 | Torassa et al. ..................... 220/337 |
| 4,357,849 | 3/1983 | Hanifl . |
| 4,580,688 | 4/1986 | Harris et al. . |
| 4,714,168 | 12/1987 | Johnson et al. ................. 206/366 X |
| 4,715,498 | 12/1987 | Hanifl . |
| 4,736,860 | 4/1988 | Bemis . |
| 4,779,728 | 10/1988 | Hanifl et al. ....................... 206/366 |
| 4,802,579 | 2/1989 | Hall et al. ........................... 206/366 |
| 4,874,103 | 10/1989 | Quisenberry et al. .............. 220/254 |
| 4,890,733 | 1/1990 | Anderson . |
| 5,076,429 | 12/1991 | Patrick et al. ...................... 206/370 |
| 5,080,251 | 1/1992 | Noack ................................ 220/335 |
| 5,154,345 | 10/1992 | Shillington ...................... 220/254 X |
| 5,183,156 | 2/1993 | Bruno ................................ 206/366 |
| 5,240,108 | 8/1993 | Tonna ................................ 206/366 |

Primary Examiner—Allan N. Shoap
Assistant Examiner—Vanessa Caretto
Attorney, Agent, or Firm—Young & Thompson

[57] ABSTRACT

A lid (2) for a closed container incorporates an opening which can be closed by a door (5) provided with side walls (18) so that even when the door is open, the only access to the interior of the container is through a slot (8) in a wall (7) of the door unit. Needles or other sharps may be introduced through the opening (8) into the container for safe storage. When the door (5) is pushed down to close the opening, a two-part live hinge formed by grooves (14) acts to bias the door into the closed position. Re-opening is achieved by pressing on the flange (6) incorporating the grooves (14). A flap (21) provides a secondary closure device.

7 Claims, 4 Drawing Sheets

SHARPS DISPOSAL CONTAINER WITH A PIVOTED CLOSURE DOOR

In a hospital environment, for example, there is a need for the safe disposal of sharps, particularly syringe needles, in such a way that the user will not be in danger of coming into contact with the items disposed of which could cause injury or the inadvertent spread of disease. It is therefore an object of this invention to provide a container which will enable sharps to be disposed of safely.

According to the present invention there is provided a sharps disposal container having a closed lid with a pivotally arranged door in the top surface of the lid, the door being rotatable about the pivot to raise a wall depending from the door above the lid surface, whilst downwardly projecting skirts from the lid and from the door maintain the closed integrity of the container during pivoting of the door, the only access to the interior of the container being an opening in the wall for receipt of sharps when that wall is raised.

With such a container, when the door is retracted into the lid of a container the contents will be totally contained and inaccessible. When the door is raised to expose the opening in the wall of the door, the contents are still safely retained within the container but the exposed opening allows further sharps to be inserted.

In the preferred arrangement the opening in the wall is keyhole shaped, ideally of stepped form for receipt of needles of differing sizes.

The wall is best provided at one end of the pivoting door. It is much preferred that the door should incorporate a releasable sprung flange for biasing the door into a closed position. This will ensure that the door does not open inadvertently when the closed container is being carried around. In this arrangement the flange is ideally at one end of a double hinged flexible plate forming part of the door top surface.

The container design may advantageously be modified such that a flap is pivotally attached to the lower end of said wall and acts as an auxiliary internal closure member for the opening in which the door is located. Ideally stop members on the skirt depending from the lid limit the extent of opening of the flap and cause the flap to be pressed against the under face of the door to close the communication between said opening and the interior of the container, when the door is closed.

For ease of assembly, the container will be formed with a base part and a lid part, the lid of the container being interlocked by rim flanges to the base of the container to create a liquid tight seal.

The invention may be performed in various ways and a preferred embodiment thereof will now be described with reference to the accompanying drawings in which.

Figure 1:
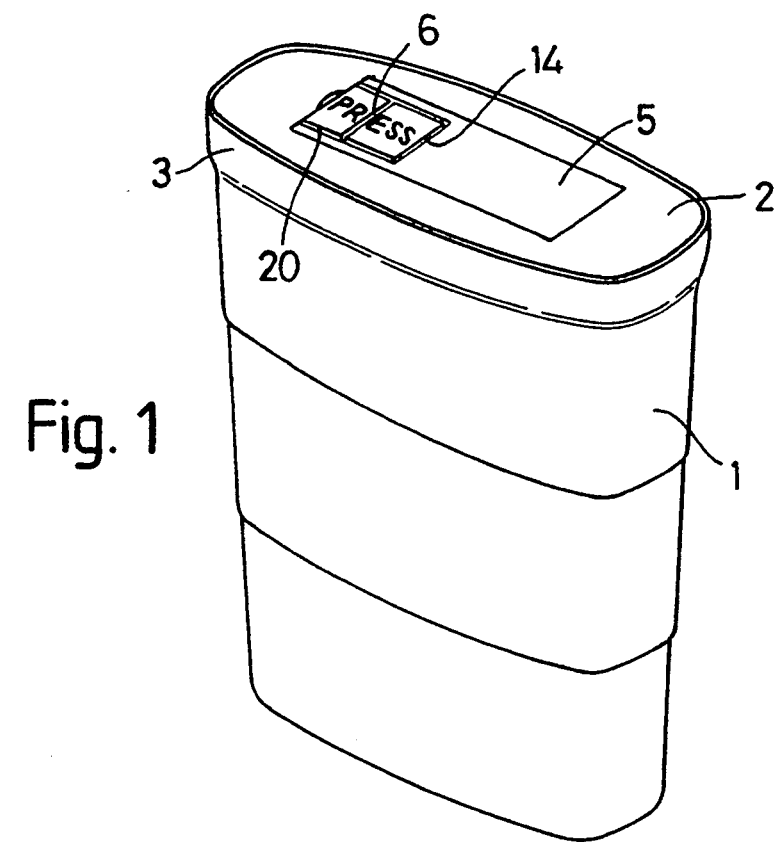
FIGS. 1 and 2 are perspective views of a sharps disposal container of this invention in the closed and open conditions respectively.
Figure 2:
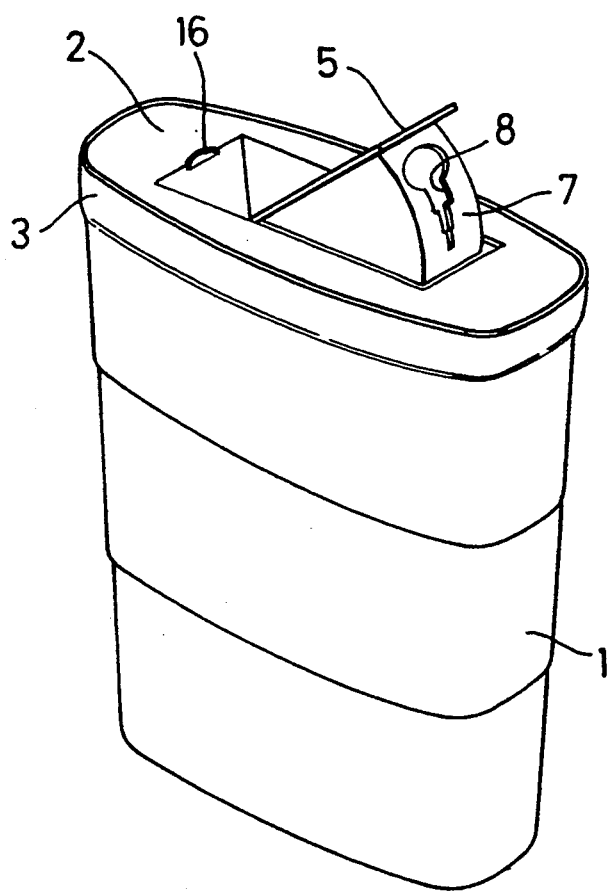
Figure 3:
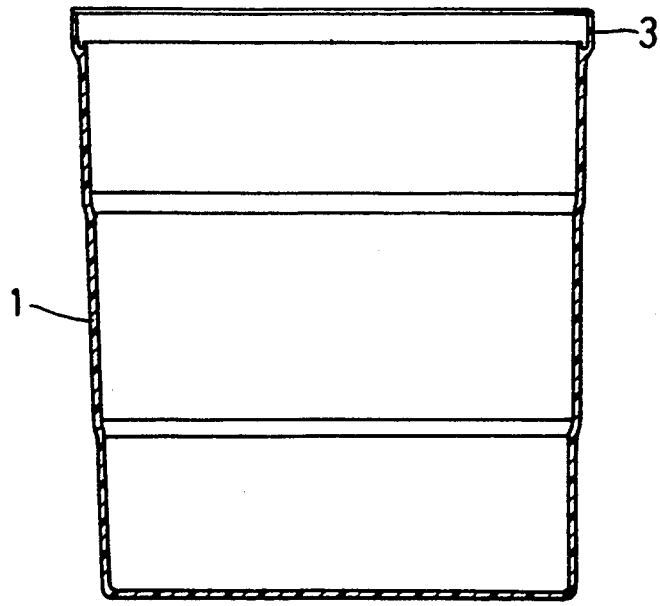
FIG. 3 is a vertical section through the base of the container.
Figure 4:
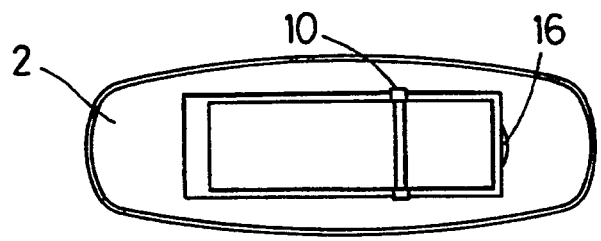
FIGS. 4 and 5 are plan and vertical sections respectively through the lid portion of the container.
Figure 5:
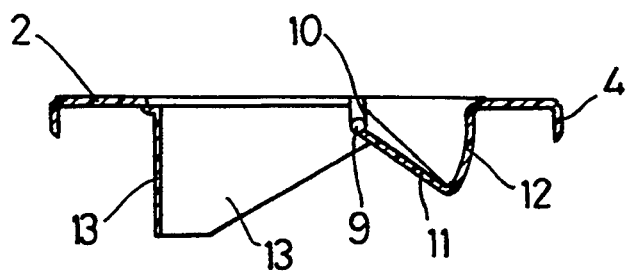
Figure 6:
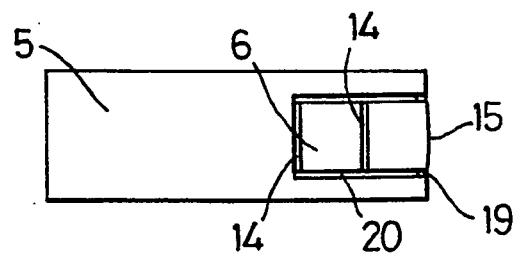
FIGS. 6 to 9 are plan, side, vertical section and end views respectively of a door part of the container.
Figure 7:
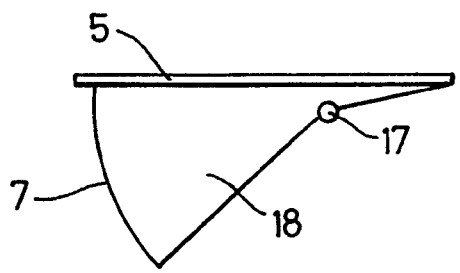
Figure 8:
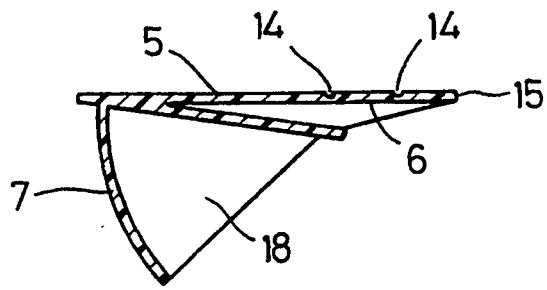
Figure 9:
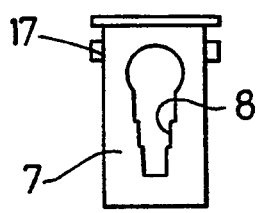

The container shown in FIGS. 1 and 2 has a base part 1 onto which is fitted a lid 2 by means of interlocking rim portions 3 and 4 as shown in FIGS. 3 and 5. Within the lid 2 is door 5 which is pivotally mounted so that when pressure is applied to a flange 6 the door 5 will pivot to expose an end wall 7 incorporating a keyhole slot 8 for receipt of needles of varying sizes from hypodermic syringes.

The door construction is shown in greater detail in FIGS. 4 to 9 of the drawings. As can be seen from FIG. 5 in particular a pivot receipt slot 9 is formed at the end of a tapered pivot guide 10. Extending down from the pivot slot 9 is a finger guard defined by walls 11 and 12 which receives the one end of the door 5 which incorporates the flange 6. A skirt 13 also extends down at the other side of the opening in the lid to prevent needles within the container from projecting up into the mechanism at the side of the door 5.

The flange 6 is formed as a two-part live hinge by forming grooves 14 in the moulded plastics material from which the door is constructed. When pressure is applied to the flange 6 the hinge members flex so as to retract an extending edge 15 which can then pass over a step 16 in the lid 2 (FIG. 2) so that the door can be tilted about the pivot 17 in pivot slots 9. This exposes the end wall 7 and the integrity of the closure of the box is maintained by side walls 18 on the door. When the end of the door nearest to the wall 7 is pressed downwardly, the flange 6 returns to its normal position and webs 19 at the ends of slots 20 cause the retractable edge 15 to spring back into the step 16 to hold the door in a closed condition.

Figure 10:
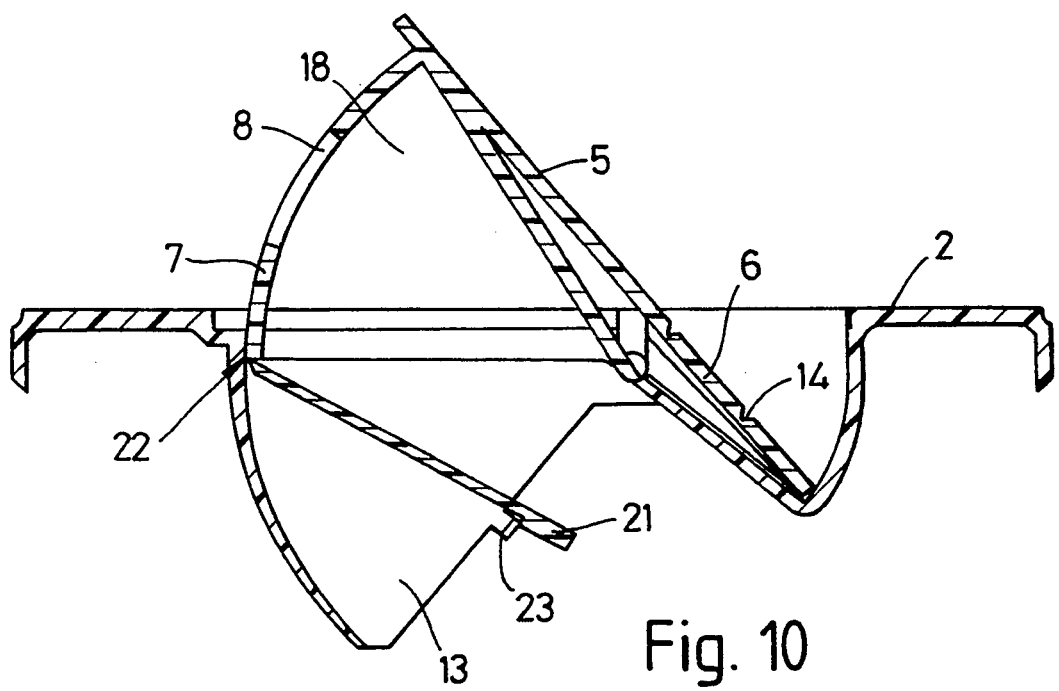
FIGS. 10 and 11 are vertical sections through an alternative form of door for a container in the open and closed conditions respectively.
Figure 11:
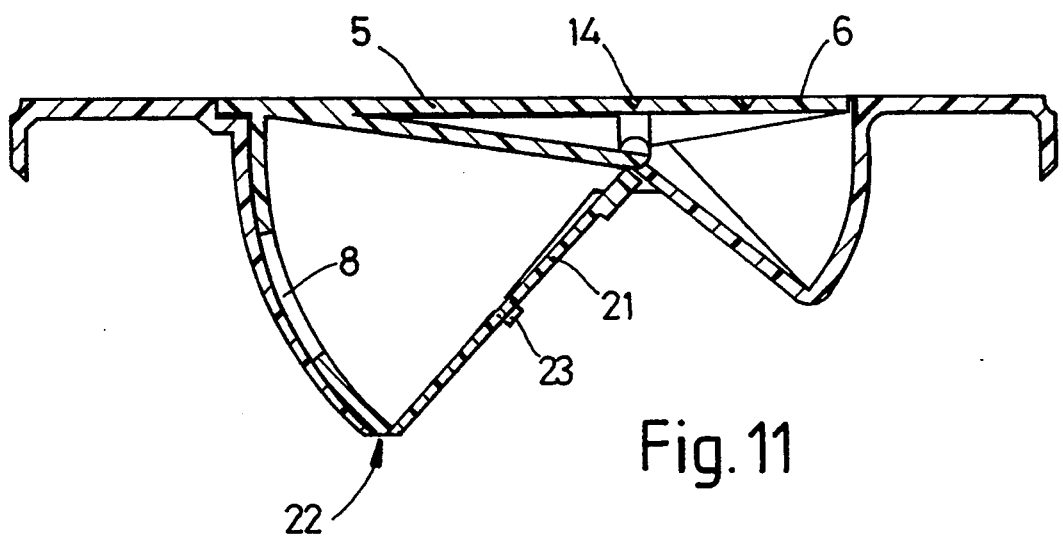

In the arrangement shown in FIGS. 10 and 11 the door 5 is provided with a flap or gate 21 which is connected to the lower end of the wall 7 by an integral very light hinge 22. The flap 21 can move freely on this hinge but at the far end its movement is restricted by two pegs 23 moulded onto the skirts 13. This provides a more restricted access to the interior of the container for the sharps. However, when the door 5 is closed the pegs 23 act to press the flap 21 up against the inner end of the door 5 so that nothing can pass into the operating area of the door from the interior of the container to jam the mechanism (see FIG. 11). When the door is open (FIG. 10), should the container fall over, the flap 21 would close so as to block the communication of the entry slots 8 with the interior of the container and thus prevent anything from falling out. Once the container is placed upright again the flap 21 will fall down to provide the necessary access.

I claim:

1. A sharps disposal container, comprising a container body defining an interior and closed by a lid having side and top walls, said top wall defining an opening, a door mounted on a pivot on said lid in said opening, an end wall depending from said door and defining an access opening, the door being swingable about said pivot to raise said end wall above said top wall, a first pair of downwardly projecting skirts depending from the door and connected to said end wall, and a second pair of downwardly projecting skirts depending from said lid, wherein said two pairs of skirts together ensure that the container body interior is closed during pivoting of said door, except for access to said interior through said access opening in said end wall for receipt of sharps when the end wall is raised, said end wall having a lower edge, and a flap pivotally attached to said lower edge to act as an auxiliary internal closure member for said opening within which said door is located.

2. A container according to claim 1, wherein the access opening in the end wall is keyhole shaped, preferably of stepped form for receipt of needles of differing sizes.

3. A container according to claim 1, wherein the access wall is at one end of the pivoting door.

4. A container according to claim 1, wherein said door is formed to define a releasable sprung flange for biasing the door into a closed position.

5. A container according to claim 4, wherein the flange is at one end of a double hinged flexible plate forming part of the door.

6. A container according to claim 1, wherein said second pair of projecting skirts incorporates stop members, said door has an under face, and said flap cooperates with said stop members such that, when the door is opened, the stop members limit the extent of opening of the flap and, when said door is closed, the stop members cause the flap to be pressed against the under face of said door to close off the under face of the door from the interior of the container body.

7. A container according to claim 1, wherein rim flanges are formed on said container body and the side wall of said lid is interlocked to the container body by said rim flanges to create a liquid tight seal.

* * * * *